United States Patent [19]

Mues et al.

[11] 4,199,593

[45] Apr. 22, 1980

[54] COMBATING ARTHROPODS WITH 5-(3,4-METHYLENEDIOXYBENZYL)-DIOXOLANES AND SYNERGISTIC COMPOSITIONS THEREWITH

[75] Inventors: Volker Mues, Wuppertal; Wolfgang Behrenz, Overath; Gebhard Rauleder, Duesseldorf; Helmut Waldmann, Leverkusen, all of Fed. Rep. of Germany

[73] Assignee: Bayer Aktiengesellschaft, Leverkusen, Fed. Rep. of Germany

[21] Appl. No.: 930,282

[22] Filed: Aug. 2, 1978

[30] Foreign Application Priority Data

Aug. 10, 1977 [DE] Fed. Rep. of Germany ....... 2736017

[51] Int. Cl.² .................... A01N 9/28; C07D 317/44
[52] U.S. Cl. .................... 424/282; 260/340.5 R; 424/203
[58] Field of Search .................. 260/340.5 R; 424/282

[56] References Cited

U.S. PATENT DOCUMENTS 3,008,968   11/1961   Beets et al. .................... 260/340.5 R

OTHER PUBLICATIONS

Chem. Abstracts 87:146963j, with subject index vol. 87–876CS.
Bergmann et al., Israel Journ. of Entomology, vol. XI, 1976, pp. 15–31.

Primary Examiner—Ethel G. Love
Attorney, Agent, or Firm—Sprung, Felfe, Horn, Lynch & Kramer

[57] ABSTRACT

5-(3,4-Methylenedioxybenzyl)-dioxolanes of the formula

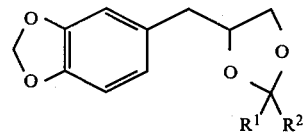

in which
$R^1$ and $R^2$ each independently is H, alkyl, alkenyl, alkynyl and aryl, or together are an alkylene radical, which possess arthropodicidal properties, and which form synergistic compositions with carbamates, carboxylic acid esters, phosphoric and phosphonic acid esters, cycloalkanes and halogenoalkanes.

14 Claims, No Drawings

COMBATING ARTHROPODS WITH 5-(3,4-METHYLENEDIOXYBENZYL)-DIOXOLANES AND SYNERGISTIC COMPOSITIONS THEREWITH

The present invention relates to and has for its objects the provision of particular new 5-(3,4-methylenedioxybenzyl)-dioxolanes which possess arthropodicidal properties, active compositions in the form of mixtures of such compounds with solid and liquid dispersible carrier vehicles and/or with synergistic agents, and methods for producing such compounds and for using such compounds in a new way especially for combating pests, e.g. arthropods, with other and further objects becoming apparent from a study of the within specification and accompanying examples.

Synergistic mixtures of carbamates, for example 2-isopropoxy-phenyl N-methylcarbamate, or of phosphoric acid esters, for example O,O-diethyl-O-[2-isopropyl-4-methyl-pyrimidin-6-yl]-thionophosphoric acid esters, or of naturally occurring or synthetic pyrethroids with piperonyl ethers, for example α-[2-(2-butoxy-ethoxy)-ethoxy]-4,5-methylenedioxy-2-propyl-toluene, are already known (see Bull. Wld. Health Org. 1966, 35, pages 691–708; Schrader, G., Die Entwicklung neuer insektizider Phosphorsaureester (The Development of New Insecticidal Phosphoric Acid Esters) 1963, pages 158; and Perkov, W., Die Insektizide (Insecticides), 1966, pages 516–524). However, the activity of these synergistic active compound combinations is not satisfactory. Only α-[2-(2-butoxy-ethoxy)-ethoxy]-4,5-methylenedioxy-2-propyl-toluene has hitherto achieved a certain practical importance.

The present invention now provides, as new compounds, the benzodioxole derivatives of the general formula

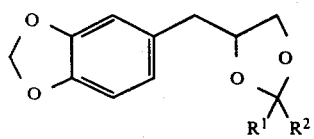

(I)

in which
R¹ and R², which can be identical or different, each represent H, alkyl, alkenyl, alkynyl or aryl or
R¹ and R² together represent an alkylene group.

Preferably, R¹ and R² each represent hydrogen, straight-chain or branched alkyl or alkenyl with up to 10 carbon atoms, or optionally substituted phenyl or R¹ and R² together represent a straight-chain or branched alkylene chain with up to 10 carbon atoms.

Examples which may be mentioned are: 5-(3,4-methylenedioxybenzyl)-dioxolane, 2-methyl-5-(3,4-methylenedioxybenzyl)-dioxolane, 2-ethyl-5-(3,4-methylenedioxybenzyl)-dioxolane, 2-n-propyl-5-(3,4-methylenedioxybenzyl)-dioxolane, 2-i-propyl-5-(3,4-methylenedioxybenzyl)-dioxolane, 2-n-butyl-5-(3,4-methylenedioxybenzyl)-dioxolane, 2-i-butyl-5-(3,4-methylenedioxybenzyl)-dioxolane, 2-t-butyl-5-(3,4-methylenedioxybenzyl)-dioxolane, 2-allyl-5-(3,4-methylenedioxybenzyl)-dioxolane, 2-methallyl-5-(3,4-methylenedioxybenzyl)-dioxolane, 2-crotyl-5-(3,4-methylenedioxybenzyl)-dioxolane, 2-ethynyl-5-(3,4-methylenedioxybenzyl)-dioxolane, 2-phenyl-5-(3,4-methylenedioxybenzyl)-dioxolane, 2-(3,4-methylenedioxyphenyl)-5-(3,4-methylenedioxybenzyl)-dioxolane, 2,2-dimethyl-5-(3,4-methylenedioxybenzyl)-dioxolane, 2-methyl-2-ethyl-5-(3,4-methylenedioxybenzyl)-dioxolane, 2-methyl-2-n-propyl-5-(3,4-methylenedioxybenzyl)-dioxolane, 2-methyl-2-i-propyl-5-(3,4-methylenedioxybenzyl)-dioxolane, 2-methyl-2-n-butyl-5-(3,4-methylenedioxybenzyl)-dioxolane, 2-methyl-2-i-butyl-5-(3,4-methylenedioxybenzyl)-dioxolane, 2-methyl-2-t-butyl-5-(3,4-methylenedioxybenzyl)-dioxolane, 2,2-diethyl-5-(3,4-methylenedioxybenzyl)-dioxolane, 2,2-di-n-propyl-5-(3,4-methylenedioxybenzyl)-dioxolane, 2,2-di-n-butyl-5-(3,4-methylenedioxybenzyl)-dioxolane, 2-methyl-2-phenyl-5-(3,4-methylenedioxybenzyl)-dioxolane, 2-spirocyclopentane-5-(3,4-methylenedioxybenzyl)-dioxolane, 2-spirocyclohexane-5-(3,4-methylenedioxybenzyl)-dioxolane and 2-(2,4,4-trimethylspirocyclohexane)-5-(3,4-methylenedioxybenzyl)-dioxolane.

The present invention also provides a process for the preparation of a compound of the formula (I), in which a compound of the general formula

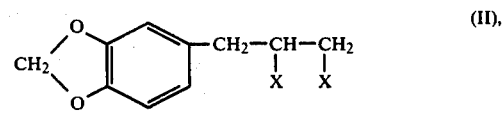

(II), in which
each X represents OH or
both X's together represent —O—,
is reacted with a carbonyl compound of the general formula

(III), in which
R¹ and R² have the meanings stated above,
optionally in the presence of a diluent.

The compounds of the formula (II) used as starting compounds for the preparation of the benzodioxole derivatives according to the invention are 3-(3,4-methylenedioxyphenyl)-propane-1,2-diol and 3,4-methylenedioxybenzylethylene oxide. Both compounds are known, as are the carbonyl compounds of the formula (III).

The process for the preparation of the compounds according to the invention is optionally carried out using a suitable diluent. Possible diluents are virtually all the inert organic solvents, especially aliphatic and aromatic, optionally chlorinated, hydrocarbons, such as benzene, toluene, xylene, methylene chloride, chloroform and carbon tetrachloride.

In the case where X represents OH, the reaction is carried out in the presence of an acid catalyst, for example sulphuric acid or p-toluenesulphonic acid, and in the case where the two radicals X represent an oxygen atom, the reaction is carried out in the presence of a catalyst such as boron trifluoride.

The reaction temperature can be varied within a relatively wide range. In general, the reaction is carried out at about 25° to 150° C., preferably about 70° to 120° C.

In general, the reaction is allowed to proceed under normal pressure.

If 3-(3,4-methylenedioxyphenyl)-propane-1,2-diol is used as the starting material, the reactants are preferably employed in equimolar amounts. An excess of one or the other reactant brings no significant advantages. In general, the two reactants are reacted in one of the solvents indicated, in the presence of an acid catalyst, at the temperatures indicated. The water thereby formed is removed by azeotropic distillation.

If 3,4-methylenedioxybenzylethylene oxide is used as the starting component, a preferred embodiment is that in which the carbonyl compound is employed in excess and thus serves as reactant and solvent. The reaction is preferably carried out in the presence of one of the catalysts indicated at the temperature indicated. After the reaction has ended, the reaction mixture is worked up in the customary manner by extracting by shaking with an organic solvent, washing the extract, drying the organic phase and distilling off the solvent.

The compounds according to the invention are characterized by their boiling point.

The present invention also provides an arthropodicidal composition containing as active ingredient (1) a benzodioxole derivative (I) and (2) at least one compound selected from (A) carbamates, (B) carboxylic acid esters (including the naturally occurring and synthetic pyrethroids), (C) phosphoric and phosphonic acid esters, (D) cycloalkanes and (E) halogenoalkanes, alone or in admixture with a solid or liquid or liquefied gaseous diluent or carrier.

These compositions have a particularly high insecticidal and acaricidal action.

The present invention also provides a method of combating arthropods (especially insects or acarids) which comprises applying to the arthropods, or to a habitat thereof, a composition as defined above.

The present invention also provides crops whenever protected from damage by arthropods by their being grown in areas in which immediately prior to and/or during the time of the growing a composition as defined above was applied.

Preferred carbamates (A) are those of the general formula

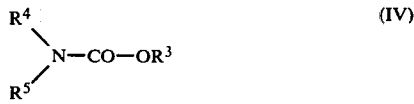

(IV)

in which

R³ represents aryl, a heterocyclic radical or an oxime radical,

R⁴ represents hydrogen or alkyl with 1 to 4 carbon atom and

R⁵ represents alkyl or alkylcarbonyl with 1 to 6 carbon atoms in the alkyl radical [which can be optionally substituted by hydroxyl or methylthio] or the radical —S—Z,
wherein Z represents an aliphatic radical with 1 to 4 carbon atoms [which is optionally substituted by halogen] (especially CCl₃ and CF₃), an aryl radical (especially phenyl) [which is optionally substituted by (preferably) nitrile, halogen (especially chlorine), methyl, trihalogenomethyl, trifluoromethylmercapto or nitro], methoxycarbonyl or the radical

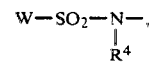

wherein

W represents alkyl, halogenoalkyl, alkylamino, dialkylamino each with up to 4 carbon atoms per alkyl radical, or an alkyl radical (which is optionally substituted by (preferably) halogen, trihalogenomethyl, nitrile, meth methyl or nitro).

Particularly preferred carbamates (IV) are those in which

R³ represents phenyl or naphthyl [either of which is optionally substituted by alkyl, alkenyl, alkoxy, alkylmercapto or alkylthioalkylene with up to 5 carbon atoms in each case, dialkylamino or dialkenylamino with up to 3 carbon atoms per alkyl or alkenyl part, halogen (especially chlorine), dioxolanyl or the radical —N=CH—N(C₁₋₄-alkyl)₂], or R³ represents, 2,3-dihydrobenzofuranyl, benzodioxole, benzothienyl, pyrimidinyl or pyrazolyl [any of which is optionally substituted by C₁₋₄-alkyl (especially methyl) or dialkylamino with 1 to 4 carbon atoms per alkyl part] or R³ represents an oxime radical of the general formula

(IVa)

in which

R⁶ and R⁷, which may be identical or different, each represent alkyl, cycloalkyl, alkenyl, alkynyl, alkoxy, alkylmercapto, alkoxycarbonyl, carbonylamide or alkylmercaptoalkyl with up to 5 carbon atoms in each case, nitrile, aryl (especially phenyl), an optionally substituted heterocyclic radical or alkyl which is substituted by a heterocyclic radical, or R⁶ and R⁷ together represent a dioxolanyl or dithiolanyl radical which is optionally substituted by C₁₋₄-alkyl.

The following carbamates may be mentioned in particular: 2-methylphenyl, 2-ethylphenyl, 2-n-propylphenyl, 2-methoxyphenyl, 2-ethoxyphenyl, 2-iso-propoxyphenyl, 4-methylphenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-[1,3-dioxolan-2-yl-phenyl] and 2,2-dimethyl-1,3-benzodioxol-4-yl N-methylcarbamate and the corresponding N-methyl-N-acetyl-, N-methyl-N-trifluoromethylthio-, N-methyl-N-dichloro-monofluoromethylthio- and N-methyl-N-dimethylaminothio-carbamates.

Preferred carboxylic acid esters (B) are those of the general formula

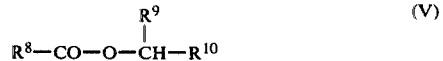

(V)

in which

R⁸ represents alkyl, aralkyl, aryl or cycloalkyl, each of which can be optionally substituted, R⁹ represents hydrogen, alkyl, halogenoalkyl, alkenyl, alkynyl or nitrile and $R^{10}$ represents aryl or a heterocyclic radical, or together with $R^9$ forms an optionally substituted cyclopentenone ring.

Especially preferred carboxylic acid esters (V) are those in which $R^8$ represents alkyl with 1 to 6 carbon atoms [which is optionally substituted by optionally substituted phenyl], cyclopropyl [which is optionally substituted by alkyl, alkenyl, halogenoalkyl or halogenoalkenyl with up to 6 carbon atoms in each case] or phenyl which is optionally substituted, and/or $R^9$ represents hydrogen alkyl with 1 to 6 carbon atoms, halogenoalkyl with 1 to 4 carbon atoms and up to 3 halogen atoms, nitrile or ethynyl, and/or $R^{10}$ represents phenyl [which is optionally substituted by $C_{1-4}$-alkyl, halogen (especially fluorine or chlorine), optionally substituted phenoxy or optionally substituted benzyl], furanyl, tetrahydrophthalimido or benzodioxole [any of which is optionally substituted by halogen (especially chlorine), alkyl or alkenyl with up to 4 carbon atoms or benzyl] or cyclopentenone [which is optionally substituted by $C_{1-4}$-alkyl, furfuryl, or $C_{2-5}$-alkenyl].

The naturally occurring pyrethroids are also particularly preferred.

The following carboxylic acid esters may be mentioned in particular: acetic acid 1-(3,4-dichlorophenyl)-2,2,2-trichloroethyl ester, 2,3,4,5-tetrahydrophthalimidomethyl chrysanthemate and (5-benzyl-3-furyl)-methyl 2,2-dimethyl-3-(2-methyl-propenyl)-cyclopropane-carboxylate.

Preferred phosphoric and phosphonic acid esters (C) are those of the general formula

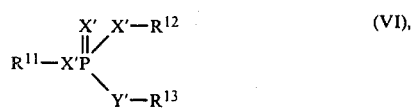 (VI), in which each X', independently of any other, represents O or S, Y' represents O, S, —NH— or a direct bond between the central P atom and the radical $R^{13}$, $R^{11}$ and $R^{12}$, which may be identical or different, each represent alkyl or aryl and $R^{13}$ represents alkyl, aryl, heteroaryl, aralkyl, alkenyl, dioxanyl, an oxime radical or a radical identical to that to which it is bonded.

Especially preferred phosphoric acid esters (VI) are those in which $R^{11}$ and $R^{12}$, which may be identical or different, each represent $C_{1-4}$-alkyl or phenyl and $R^{13}$ represents alkyl with 1 to 4 carbon atoms [which is optionally substituted by halogen, hydroxyl, nitrile, optionally substituted phenyl, amidocarbonyl, alkylsulphonyl, alkylsulphoxy, alkylcarbonyl, alkoxy, alkylmercapto or alkoxycarbonyl], alkenyl with up to 4 carbon atoms [which is optionally substituted by halogen, optionally halogen-substituted phenyl or alkoxycarbonyl] or an oxime radical of the general formula

 (IVa)

wherein $R^6$ and $R^7$ have the meanings stated above (but especially cyano or phenyl), or $R^{13}$ represents dioxanyl which is substituted by a radical identical to that to which $R^{13}$ is bonded, or $R^{13}$ represents a radical identical to that to which it is bonded, or $R^{13}$ represents phenyl [which is optionally substituted by methyl, nitro, nitrile, halogen or methylthio] or $R^{13}$ represents a hetero-aromatic (such as pyridine, quinoline, quinoxaline, pyrimidine, diazinone or benzo-1,2,4-triazine) which is optionally substituted by $C_{1-4}$-alkyl or halogen.

The following phosphoric and phosphonic acid esters may be mentioned in particular: O,O-dimethyl- or O,O-diethyl-O-(2,2-dichloro- or 2,2-dibromo-vinyl)-phosphoric acid ester, O,O-diethyl-O-(4-nitro-phenyl)-thionophosphoric acid ester, O,O-dimethyl-O-(3-methyl-4-methylthio)-thionophosphoric acid ester, O,O-dimethyl-O-(3-methyl-4-nitro)-thionophosphoric acid ester, O-ethyl-S-n-propyl-O-(2,4-dichlorophenyl)-thionophosphoric acid ester, O-ethyl-S-n-propyl-O-(4-methylthio-phenyl)-thionophosphoric acid ester, O,O-dimethyl-S-[4-oxo-1,2,3-benzotriazin-3-yl-methyl]-thionothiolphosphoric acid ester, O-methyl-O-[2-isopropyl-6-methoxypyrimidin-4-yl]-thionomethanephosphonic acid ester, O,O-diethyl-O-[2-iso-propyl-6-methyl-pyrimidin-4-yl]-thionophosphoric acid ester, O,O-diethyl-O-[3-chloro-4-methylcoumarin-7-yl]-thionophosphoric acid ester, O,O-dimethyl-2,2,2-trichloro-1-hydroxy-ethanephosphonic acid ester and O,O-dimethyl-S-(methylcarbamoylmethyl)-thionophosphoric acid ester.

Preferred cycloalkanes (D) are those of the general formula

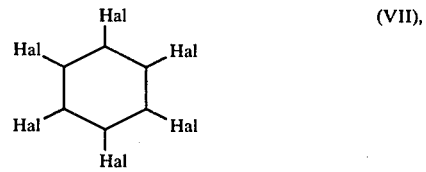 (VII), in which

Hal denotes halogen, preferably chlorine.

1,2,3,4,5,6-Hexachlorohexane may be mentioned in particular.

Preferred halogenoalkanes (E) are those of the general formula

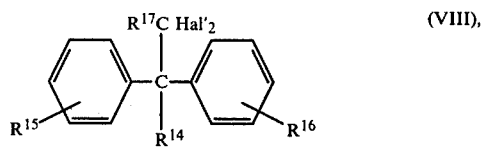 (VIII), in which

Hal' represents chlorine or bromine, $R^{14}$ represents hydrogen or hydroxyl, $R^{15}$ and $R^{16}$, which may be identical or different, each represent halogen, alkyl or alkoxy and $R^{17}$ represents hydrogen or halogen, Especially preferred halogenoalkanes (VIII) are those in which $R^{14}$ denotes hydrogen or hydroxyl, $R^{15}$ and $R^{16}$ are identical and represent halogen, alkyl with 1 to 4 carbon atoms or alkoxy with 1 to 4 carbon atoms, and $R^{17}$ denotes halogen.

The following halogenoalkanes may be mentioned in particular: 1,1,1-trichloro-2,2-bis-(4-chloro- or 4-methoxyphenyl)-ethane, 1,1,1-trichloro-2-hydroxy-2,2-bis-(4-chlorophenyl)-ethane and 1,1-dichloro-2,2-bis-(4-ethylphenyl)-ethane.

Surprisingly, the insecticidal and/or acaricidal action of such active compound combinations is considerably higher than the action of the individual components or than the sum of the actions of the individual components. Furthermore, it is considerably higher than the action of an active compound combination containing the known synergistic agent piperonyl butoxide.

In addition, the benzodioxole derivatives according to the invention exhibit excellent synergistic activity not only with one class of active compounds, but with active compounds from diverse chemical groups of substances.

The benzodioxole derivatives according to the invention thus represent a valuable enrichment of the art. Furthermore, the benzodioxole derivatives according to the invention exhibit good properties with respect to inhibiting the development of arthropods, especially insects.

The weight ratios of the groups of active compounds can vary within relatively wide ranges. In general, the benzodioxole derivative (1) and the other active compounds (2) are employed in a ratio of about 0.1:10 to 10:0.1. However, weight ratios of about 0.5:1.0 to 3.0:1.0 have proved particularly suitable.

These active compound combinations not only result in a rapid knock-down action but also result in the lasting destruction of arthropod pests, especially insects and acarids, which are encountered in agriculture, in forestry, in the protection of stored products and of materials, and in the hygiene field. They are active against normally sensitive and resistant species and against all or some stages of development.

The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and *Ceratophyllus spp.;* from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granxles, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compounds, preferably from 0.5 to 90 percent by weight.

The active compounds according to the invention may be used in the form of their formulations of the types that are commercially available or in the use forms prepared from these formulations.

The active compounds content of the use forms prepared from the formulations of the types that are commercially available can vary within wide ranges. The active compounds concentration of the use forms can be from 0.0000001 to 100% by weight of active compounds, preferably from 0.01 to 10% by weight.

The compounds may be employed in a customary manner appropriate for the particular use forms.

The novel compounds may be prepared as in the following illustrative example:

EXAMPLE 1

General Preparative Processes (A) 0.1 mol of 3-(3,4-methylenedioxyphenyl)-propane-1,2-diol was boiled with 0.1 mol of the appropriate carbonyl compound and 0.5 g of p-toluenesulphonic acid in 300 ml of benzene, using a water separator, until the reaction had ended. The reaction mixture was cooled, washed with dilute sodium hydroxide solution in order to remove the catalyst, and then with water, and dried over $Na_2SO_4$, the solvent was stripped off and the residue was distilled.

(b) 0.1 mol of 3,4-methylenedioxybenzyl-ethylene oxide was mixed with 0.5 mol of a carbonyl compound. When a few drops of boron trifluoride-etherate were added, a vigorous exothermic reaction started, which could be kept between 50° and 100° C. by cooling with an icebath. After the reaction had subsided, the reaction mixture was subsequently stirred for a further 1 hour at 60° C. and taken up in toluene, the toluene solution was washed with water until neutral and dried over $Na_2SO_4$, the solvent was stripped off and the residue was distilled.

The following compounds were obtained by these preparative processes:

TABLE 1

| Compound No. | $R^1$ | $R^2$ | Preparation route | Boiling point [°C./mm.] | Yield [%] |
|---|---|---|---|---|---|
| 1 | $CH_3$ | $CH_3$ | b | 140/3 | 72 |
| 2 | —$CH_2$—$CH_2$——$CH_2$—$CH_2$ | | b | 174/3 | 71 |
| 3 | H | $C_2H_5$ | b | 162/4 | 71 |
| 4 | H | $C_6H_5$ | b | 230/3 | 27 |
| 5 | $CH_3$ | $C_2H_5$ | b | 160/4 | 48 |
| 6 | H | H | a | 132/3 | 56 |
| 7 | H | i-$C_3H_7$ | b | 120/0.01 | 49 |
| 8 | $CH_3$ | i-$C_3H_7$ | b | 124/0.01 | 27 |
| 8 | $CH_3$ | i-$C_3H_7$ | a | 124/0.01 | 59 |
| 9 | H | t-$C_4H_9$ | b | 122/0.01 | 40 |

TABLE 1-continued

| Compound No. | $R^1$ | $R^2$ | Preparation route | Boiling point [°C./mm.] | Yield [%] |
|---|---|---|---|---|---|
| 10 | H | n-$C_3H_7$ | b | 124/0.01 | 57 |
| 11 | H | 3,4-$OCH_2O$—$C_6H_3$ | b | 250/3 | 28 |
| 12 | $CH_3$ | n-$C_3H_7$ | b | 162/3 | 33 |
| 13 | $CH_3$ | t-$C_4H_9$ | b | 100/0.1 | 35 |
| 14 | $CH_3$ | $C_6H_5$ | b | 206/4 | 32 |
| 15 | $C_2H_5$ | $C_2H_5$ | b | 160/3 | 21 |
| 15 | $C_2H_5$ | $C_2H_5$ | a | 160/3 | 63 |
| 16 | —$CH_2$—$CH_2$—$CH_2$—$CH_2$—$CH_2$— | | b | 155/0.01 | 63 |
| 17 | —CH—$CH_2$—C($CH_3$)—$CH_2$—$CH_2$— (with $CH_3$, $CH_3$) | | b | 186/3 | 52 |

The activity of the compounds of this invention is illustrated by the following examples wherein the compounds according to the present invention are each identified by the number (given in brackets) from Example 1.

The known comparison compounds are identified as follows:

(A) = 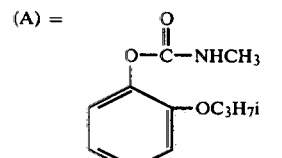

(B) = 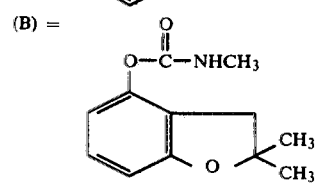

(C) = 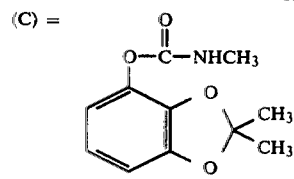

(D) = 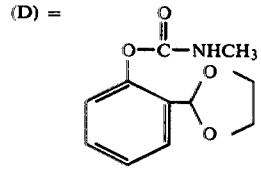

(E) = 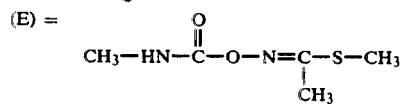

(F) = Pyrethrins as a 25% strength extract (G) = 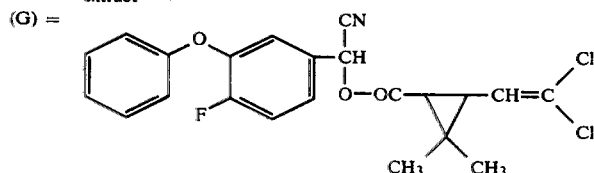

(H) = 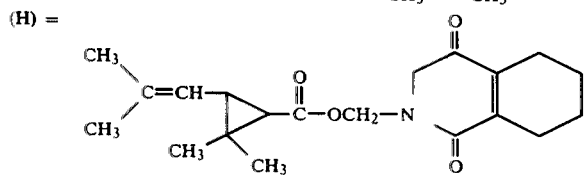

-continued

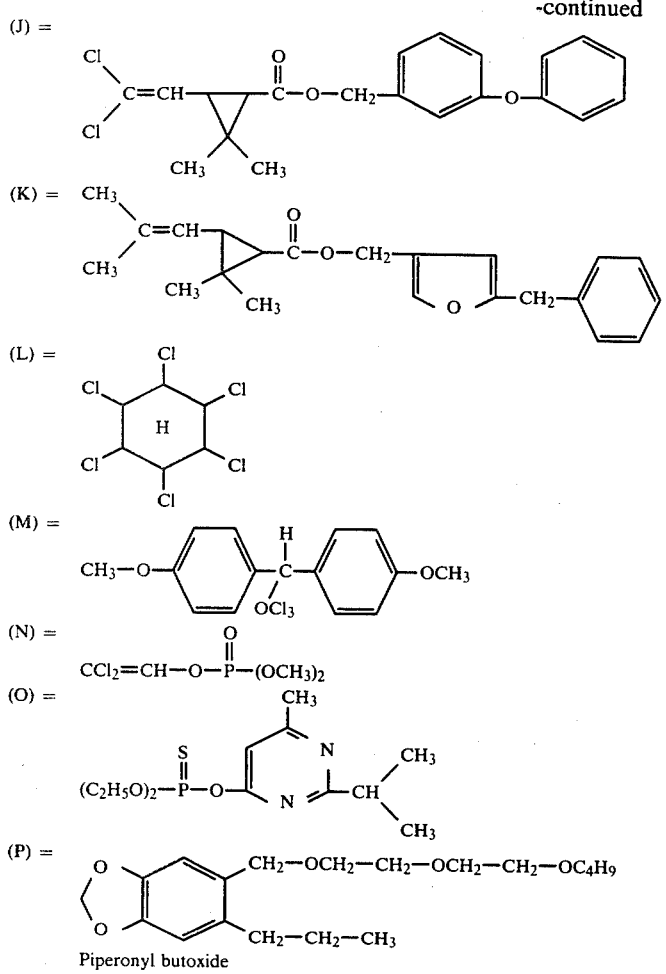

Piperonyl butoxide

EXAMPLE 2

LT$_{100}$ test

Test insects: *Musca domestica*, Weymanns strain, (resistant to carbamates and to phosphoric acid esters)

Solvent: Acetone

Solutions were prepared from the active compounds, synergistic agents and mixtures of active compounds and synergistic agents, and 2.5 ml of each solution were pipetted onto a filterpaper disc of 9.5 cm diameter in a respective Petri dish. The filterpaper adsorbed the solution. The Petri dish was left standing open until the solvent had completely evaporated. 25 test insects were then introduced into the Petri dish, and the dish was covered with a glass lid.

The condition of the test insects was checked continuously for up to 6 hours. The time required for a 100% knockdown action was determined. If the LT$_{100}$ was not reached after 6 hours, the percentage of the test insects which had been knocked down was determined.

The concentrations of the active compounds, synergistic agents and mixtures, and their actions, can be seen from the table which follows.

Table 2

LT$_{100}$ test with *Musca domestica* (Weymanns strain) resistant to phosphoric acid esters

| Active compound and/or synergistic agent | Concentration in % | LT$_{100}$ after minutes |
| --- | --- | --- |
| (A) | 1.0 | 360' = 0% |
| (B) | 1.0 | 360' = 0% |
| (C) | 1.0 | 360' = 5% |
| (D) | 1.0 | 360' = 0% |
| (E) | 0.04 | 360' = 35% |
| (F) | 0.04 | 360' = 80% |
| (G) | 0.0016 | 6 hrs = 50% |
| (H) | 0.2 | 180' |
| (J) | 0.04 | 75' |
| (K) | 0.04 | 150' |
| (L) | 1.0 | 360' = 90% |
| (M) | 1.0 | 360' = 5% |
| (N) | 0.008 | 240' |
| (O) | 0.04 | 360' = 5% |
| (P) | 1.0 | 360' = 0% |
| (1) | 0.2 | 360' = 70% |
| (2) | 0.2 | 360' = 0% |
| (3) | 0.2 | 360' = 0% |
| (4) | 1.0 | 360' = 0% |
| (5) | 0.2 | 310' = 5% |
| (6) | 1.0 | 360' = 0% |
| (7) | 1.0 | 360' = 0% |
| (8) | 1.0 | 360' = 0% |
| (9) | 1.0 | 360' = 0% |
| (A) + (P) | 0.2 + 0.2 | 360' = 90% |
| (A) + (1) | 0.04 + 0.04 | 150' |

Table 2-continued

| Active compound and/or synergistic agent | Concentration in % | LT$_{100}$ after minutes | |
|---|---|---|---|
| (A) + (3) | 0.2 + 0.2 | 180" | |
| (A) + (6) | 0.04 + 0.04 | 150' | |
| (A) + (7) | 0.2 + 0.2 | 240' | |
| (A) + (8) | 0.2 + 0.2 | 240' | |
| (A) + (9) | 0.2 + 0.2 | 180' | |
| (B) + (P) | 1.0 + 1.0 | 360' | = 90% |
| (B) + (1) | 0.04 + 0.04 | 120' | |
| (B) + (2) | 0.2 + 0.2 | 360' | |
| (B) + (3) | 0.04 + 0.04 | 240' | |
| (B) + (5) | 0.04 + 0.04 | 210' | |
| (C) + (P) | 1.0 + 1.0 | 360' | = 75% |
| (C) + (1) | 0.04 + 0.04 | 150' | |
| (C) + (3) | 1.0 + 1.0 | 180' | |
| (C) + (5) | 0.2 + 0.2 | 210' | |
| (D) + (P) | 1.0 + 1.0 | 360' | = 70% |
| (D) + (1) | 0.2 + 0.2 | 240' | |
| (D) + (3) | 1.0 + 1.0 | 180' | |
| (E) + (P) | 0.04 + 0.04 | 360' | = 95% |
| (E) + (1) | 0.04 + 0.04 | 150' | |
| (E) + (2) | 0.04 + 0.04 | 240' | |
| (E) + (3) | 0.04 + 0.04 | 150' | |
| (E) + (5) | 0.04 + 0.04 | 240' | |
| (F) + (1) | 0.04 + 0.04 | 45' | |
| (F) + (2) | 0.04 + 0.04 | 60' | |
| (F) + (3) | 0.04 + 0.04 | 60' | |
| (F) + (4) | 0.04 + 0.04 | 60' | |
| (F) + (5) | 0.04 + 0.04 | 60' | |
| (G) + (P) | 0.0016 + 0.0016 | 360' | = 70% |
| (G) + (3) | 0.0016 + 0.0016 | 105' | |
| (G) + (4) | 0.0016 + 0.0016 | 240' | |
| (H) + (P) | 0.04 + 0.04 | 90' | |
| (H) + (1) | 0.04 + 0.04 | 60' | |
| (H) + (2) | 0.04 + 0.04 | 45' | |
| (H) + (5) | 0.04 + 0.04 | 45' | |
| (J) + (P) | 0.04 + 0.04 | 75' | |
| (J) + (2) | 0.04 + 0.04 | 60' | |
| (J) + (5) | 0.04 + 0.04 | 45' | |
| (K) + (1) | 0.04 + 0.04 | 30' | |
| (K) + (2) | 0.04 + 0.04 | 30' | |
| (K) + (3) | 0.04 + 0.04 | 45' | |
| (K) + (4) | 0.04 + 0.04 | 45' | |
| (K) + (5) | 0.04 + 0.04 | 60' | |
| (L) + (P) | 1.0 + 1.0 | 360' | |
| (L) + (3) | 1.0 + 1.0 | 150' | |
| (L) + (5) | 1.0 + 1.0 | 90' | |
| (M) + (P) | 1.0 + 1.0 | 360' | = 45% |
| (M) + (1) | 1.0 + 1.0 | 210' | |
| (N) + (P) | 0.008 + 0.008 | 240' | |
| (N) + (1) | 0.008 + 0.008 | 105' | |
| (N) + (5) | 0.008 + 0.008 | 105' | |
| (O) + (P) | 0.04 + 0.04 | 360' | = 95% |
| (O) + (5) | 0.04 + 0.04 | 120' | |

It will be appreciated that the instant specification and examples are set forth by way of illustration and not limitation, and that various modifications and changes may be made without departing from the spirit and scope of the present invention.

What is claimed is:

1. 5-(3,4-Methylenedioxybenzyl)-dioxolanes of the formula

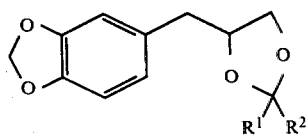

in which $R^1$ and $R^2$ each independently is H, alkyl, or phenyl, or together are an alkylene radical.

2. A compound according to claim 1, in which $R^1$ and $R^2$ each independently is hydrogen, alkyl with up to 10 carbon atoms, or phenyl, or together are alkylene with up to 10 carbon atoms.

3. A compound according to claim 1, in which said compound is 2,2-dimethyl-5-(3,4-methylenedioxybenzyl)-dioxolane of the formula

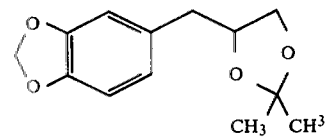

4. A compound according to claim 1, in which said compound is 2-ethyl-5-(3,4-methylenedioxybenzyl)-dioxolane of the formula

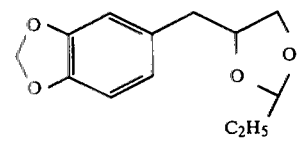

5. A compound according to claim 1, in which said compound is 2-methyl-2-ethyl-5-(3,4-methylenedioxybenzyl)-dioxolane of the formula

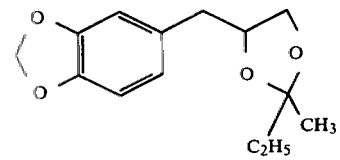

6. A compound according to claim 1, in which said compound is 5-(3,4-methylenedioxybenzyl)-dioxolane of the formula

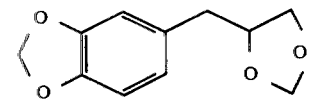

7. A compound according to claim 1, in which said compound is 2-t-butyl-5-(3,4-methylenedioxybenzyl)-dioxolane of the formula

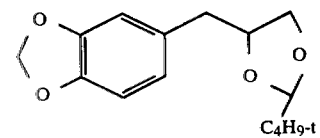

8. An arthropodicidal composition comprising an arthropodicidally effective amount of a benzodioxole derivative according to claim 1 in admixture with a diluent.

9. A composition according to claim 8, wherein the diluent comprises a synergistically effective amount of at least one compound selected from (A) carbamates, (B) carboxylic acid esters, (C) phosphoric and phosphonic acid esters, (D) cycloalkanes and (E) halogenoalkanes.

10. A composition according to claim 8, wherein the diluent comprises a synergistically effective amount of at least one compound selected from (A) carbamates of the formula

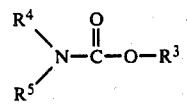

in which $R^3$ represents aryl, a heterocyclic radical or an oxime radical, $R^4$ represents hydrogen or alkyl with 1-4 carbon atoms and $R^5$ represents alkyl or alkylcarbonyl with 1-6 carbon atoms in the alkyl radical [which can be optionally substituted by hydroxyl or methylthio] or the radical —S—Z, wherein Z represents an aliphatic radical with 1 to 4 carbon atoms, [which is optionally substituted by halogen], an aryl radical, [which is optionally substituted by nitrile, halogen, methyl, trihalogenomethyl, trifluoromethylmercapto or $NO_2$], methoxycarbonyl or the radical

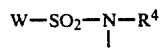

wherein

W represents alkyl, halogenoalkyl, alkylamino, dialkylamino each with up to 4 carbon atoms per alkyl radical or an aryl radical (optionally substituted by halogen, trihalogenmethyl, nitrile, methyl or nitro), (B) carboxylic acid esters of the formula

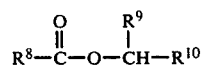

in which $R^8$ represents alkyl, aralkyl, aryl or cycloalkyl, each of which can be optionally substituted, $R^9$ represents hydrogen, alkyl, halogenoalkyl, alkenyl, alkynyl or nitrile and $R^{10}$ represents aryl or a heterocyclic radical, or $R^9$ and $R^{10}$ together form an optionally substituted cyclopentenone ring, and the naturally occurring pyrethroids, (C) phosphoric and phosphonic acid esters of the formula

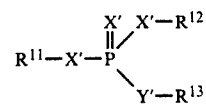

in which each X', independently of any other, represents O or S,

Y' represents O, S, —NH— or a direct bond between the central P atom and the radical $R^{13}$, $R^{11}$ and $R^{12}$, which may be identical or different, each represent alkyl or aryl and $R^{13}$ represents alkyl, aryl, heteroaryl, aralkyl, alkenyl, dioxanyl, an oxime radical or represents a radical identical to that to which it is bonded, (D) cycloalkanes of the formula

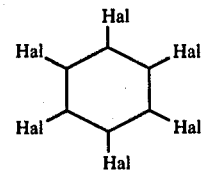

in which

Hal represents halogen, and (E) halogenoalkanes of the formula

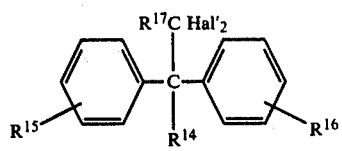

in which

Hal' represents chlorine or bromine, $R^{14}$ represents hydrogen or hydroxyl, $R^{15}$ and $R^{16}$, which may be identical or different, each represent halogen, alkyl or alkoxy and $R^{17}$ represents hydrogen or halogen.

11. A composition according to claim 10, in which $R^3$ represents phenyl or naphthyl [either of which is optionally substituted by alkyl, alkenyl, alkoxy, alkylmercapto or alkylthioalkylene with up to 5 carbon atoms in each case, dialkylamino, or dialkenylamino with up to 3 carbon atoms per alkyl or alkenyl part, halogen, dioxolanyl or the radical —N=CH—N($C_{1-4}$-alkyl)$_2$], or $R^3$ represents 2,3-dihydrobenzofuranyl, benzodioxole, benzothienyl, pyrimidinyl or pyrazolyl [each of which is optionally substituted by $C_{1-4}$-alkyl or dialkylamino with 1-4 carbon atoms per alkyl part], or $R^3$ represents an oxime radical of the general formula

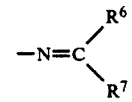

in which $R^6$ and $R^7$, which may be identical or different, each represent alkyl, cycloalkyl, alkenyl, alkynyl, alkoxy, alkylmercapto, alkoxycarbonyl, carbonylamide or alkylmercaptoalkyl with up to 5 carbon atoms in each case, nitrile, aryl, an optionally substituted heterocyclic radical or alkyl which is substituted by a heterocyclic radical, or $R^6$ and $R^7$ together form a dioxolanyl or dithiolanyl radical which is optionally substituted by $C_{1-4}$ alkyl, $R^8$ represents alkyl with 1-6 carbon atoms [which is optionally substituted by optionally halogen-substituted phenyl], cyclopropyl [which is optionally substituted by alkyl, alkenyl, halogenoalkyl or halogenoalkenyl with up to 6 carbon atoms in each case] or phenyl which is optionally substituted, $R^9$ represents hydrogen, alkyl with 1–6 carbon atoms, halogenoalkyl with 1–4 carbon atoms and up to 3 halogen atoms, nitrile or ethynyl, and $R^{10}$ represents phenyl [which is optionally substituted by $C_{1-4}$-alkyl, halogen, optionally substituted phenoxy or optionally substituted benzyl], furanyl, tetrahydrophthalimido or benzodioxole [any of which is optionally substituted by halogen, alkyl or alkenyl with up to 4 carbon atoms or benzyl] or cyclopentenone [which is optionally substituted by $C_{1-4}$-alkyl, furfuryl or $C_{2-5}$-alkenyl], $R^{11}$ and $R^{12}$, which may be identical or different, each represent $C_{1-4}$-alkyl or phenyl, and $R^{13}$ represents alkyl with 1–4 carbon atoms [which is optionally substituted by halogen, hydroxyl, nitrile, optionally substituted phenyl, alkoxy, alkylmercapto or alkoxycarbonyl], alkenyl with up to 4 carbon atoms [which is optionally substituted by halogen, optionally halogen-substituted phenyl or alkoxycarbonyl] or an oxime radical of the formula

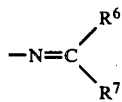

$R^{13}$ represents dioxanyl which is substituted by a radical identical to that to which $R^{13}$ is bonded, or $R^{13}$ represents a radical identical to that to which it is bonded, or $R^{13}$ represents phenyl [which is optionally substituted by methyl, nitro, nitrile, halogen or methylmercapto], or $R^{13}$ represents a hetero-aromatic structure that is optionally substituted by $C_{1-4}$-alkyl or halogen, Hal represents chlorine, $R^{15}$ and $R^{16}$ are identical and represent halogen, alkyl with 1 to 4 carbon atoms or alkoxy with 1 to 4 carbon atoms and $R^{17}$ denotes halogen, the weight ratio of the benzodioxole derivative to the diluent ranging from about 0.1:10 to 10:0.1.

12. A method of combating arthropods which comprises applying to the arthropods, or to a habitat thereof, an arthropododicidally effective amount of a compound according to claim 1.

13. The method according to claim 12, in which the compound is 2,2-dimethyl-5-(3,4-methylenedioxybenzyl)-dioxolane, 2-ethyl-5-(3,4-methylenedioxybenzyl)-dioxolane, 2-methyl-2-ethyl-5-(3,4-methylenedioxybenzyl)-dioxolane, 5-(3,4-methylenedioxybenzyl)-dioxolane, or 5-(3,4-methylenedioxybenzyl)-dioxolane.

14. The method according to claim 12, in which said compound is applied along with a synergistically effective amount of at least one compound selected from (A) carbamates, (B) carboxylic acid esters, (C) phosphoric and phosphonic acid esters, (D) cycloalkanes and (E) halogenoalkanes.

* * * * *